United States Patent [19]

Miller

[11] Patent Number: 4,727,216
[45] Date of Patent: Feb. 23, 1988

[54] DEHYDROGENATION OF ISOBUTANE OVER A ZEOLITIC CATALYST

[75] Inventor: Stephen J. Miller, San Francisco, Calif.

[73] Assignee: Chevron Research Company, San Francisco, Calif.

[21] Appl. No.: 888,543

[22] Filed: Jul. 21, 1986

Related U.S. Application Data

[63] Continuation of Ser. No. 531,134, Sep. 12, 1983, abandoned.

[51] Int. Cl.$^4$ .................. C07C 5/333; C07C 15/00
[52] U.S. Cl. .................. 585/660; 585/661; 585/656
[58] Field of Search .................. 585/656, 660, 661; 208/138; 502/223

[56] References Cited

U.S. PATENT DOCUMENTS

| | | | |
|---|---|---|---|
| 3,585,249 | 6/1971 | Cohen et al. | 585/656 |
| 3,644,200 | 2/1972 | Young | 585/661 |
| 4,124,649 | 11/1978 | Rausch | 585/660 |

Primary Examiner—Curtis R. Davis
Assistant Examiner—Chung K. Pak
Attorney, Agent, or Firm—S. R. La Paglia; T. G. DeJonghe; P. L. McGarrigle, Jr.

[57] ABSTRACT

Isobutene is produced by contacting isobutane with a sulfided, type L zeolitic catalyst containing platinum, tin, barium, and an inorganic binder. The isobutane is contacted with the catalyst in the presence of a sulfur-containing gas at a temperature of from 850° F. to 1250° F., a pressure of less than 20 psig, a liquid hourly space velocity of below 40, and an $H_2$/HC of less than 10. Preferably, the catalyst comprises: (1) a sulfided, type L zeolite containing from 8% to 10% by weight barium, from 0.6% to 1.0% by weight platinum, and tin at an atom ratio with the platinum of about 1:1; and (2) an inorganic binder of either silica, alumina, or aluminosilicates.

10 Claims, 2 Drawing Figures

PERCENT UNSELECTIVE PRODUCTS FROM $iC_4$ AT 0.75 LHSV, I ATM, AND 6 $H_2$/HC

4,727,216

DEHYDROGENATION OF ISOBUTANE OVER A ZEOLITIC CATALYST

This is a continuation of application Ser. No. 531,134, filed Sept. 12, 1983, now abandoned.

BACKGROUND OF THE INVENTION

This invention relates to the dehydrogenation of paraffins over a catalyst having a superior selectivity for dehydrogenation. More particularly, it relates to novel, sulfided composites of Group VIII metals, tin, and large-pore zeolites and their use in catalyzed paraffin dehydrogenation.

Composites of Group VIII noble metals are multifunctional in that they have substantial and concurrent activity for isomerization, cracking and dehydrogenation reactions. The isomerization and cracking activities can be inhibited by using several expedients. These expedients, however, suffer from limited catalyst life and problems with separating the dehydrogenated product from unwanted by-products. For instance, in the dehydrogenation of isobutane to form isobutene, substantial quantities of n-butane are produced, which are difficult to separate from the isobutene.

SUMMARY OF THE INVENTION

The present invention overcomes these problems by contacting a paraffinic feed with a sulfided, large-pore zeolitic, dehydrogenation catalyst, containing at least one Group VIII metal, to produce an olefin product stream. This process is especially useful for converting isobutane to isobutene.

Preferably, the paraffinic feed is contacted with the dehydrogenation catalyst in the presence of a sulfur-containing gas at a temperature of from 850° F. to 1250° F., a pressure of less than 20 psig, a liquid hourly space velocity of below 40, and an $H_2/HC$ of less than 10.

Preferably, the catalyst is a sulfided type L zeolite that contains from 8% to 10% by weight barium, from 0.6% to 1.0% by weight platinum, and tin at an atom ratio with the platinum of about 1:1.

A major advantage of this invention is that less by-products are produced, and the by-products that are produced are sufficiently different from the desired product so as to be easily removed.

BRIEF DESCRIPTION OF THE DRAWINGS

In order to facilitate the understanding of this invention, reference will now be made to the appended drawings. The drawings should not be construed as limiting the invention but are exemplary only.

DESCRIPTION OF THE PREFERRED EMBODIMENTS

Figure 1:
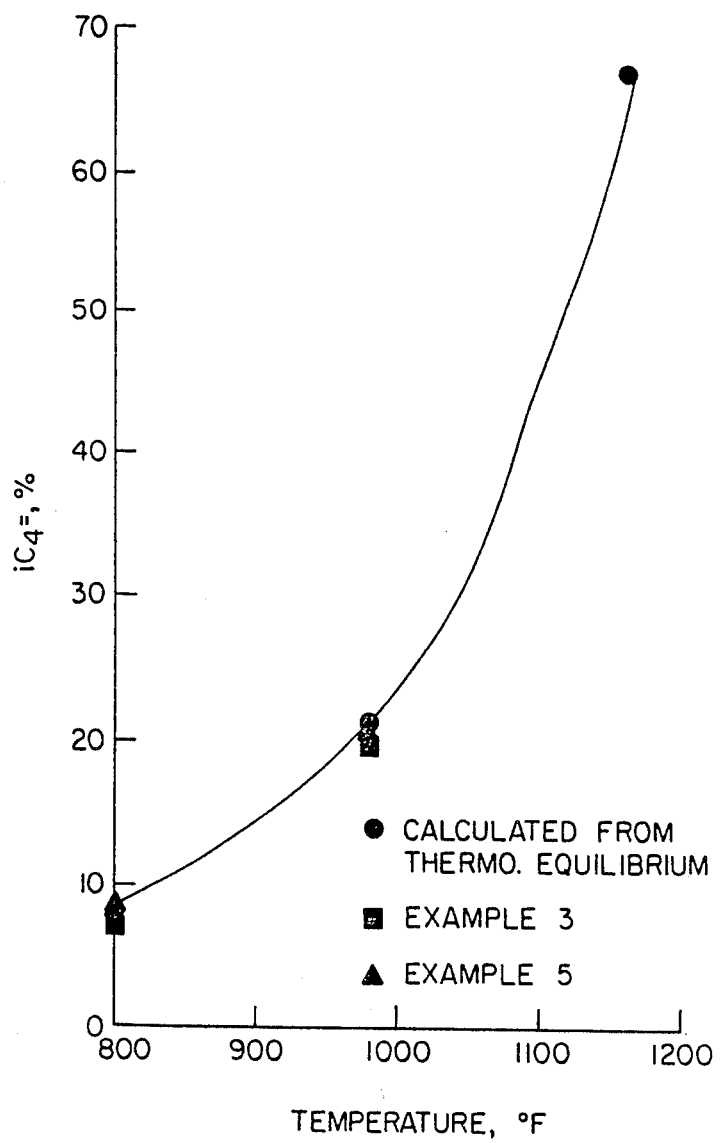
FIG. 1 is a graph showing the percent isobutene achieved with catalysts of the present invention at various temperatures.

In its broadest aspect, the present invention involves contacting a paraffinic feed with a sulfided, dehydrogenation catalyst to produce an olefin product stream. This sulfided, dehydrogenation catalyst is a large-pore zeolite containing at least one Group VIII metal.

A major element of the present invention is that the dehydrogenation catalyst is sulfided prior to use. A small amount of an oxyanion of sulfur, such as sulfate, sulfite, bisulfate, or bisulfite, associated with the catalyst helps to control the amount of cracking that occurs during dehydrogenation. The oxyanions of sulfur can be incorporated onto the catalyst composition by contacting the catalyst with the oxyanions. Suitable oxyanions of sulfur are $SO_4^-$; $SO_3^-$; $HSO_4^-$; or $HSO_3^-$.

In another embodiment, the catalyst can be sulfided on stream by passing a sulfur-containing gas, such as $H_2S$, over the catalyst.

Preferably, the paraffinic feed is contacted with the dehydrogenation catalyst in the presence of a sulfur-containing gas. In this way, the catalyst remains sulfided throughout the dehydrogenation reaction.

Preferably, the dehydrogenation catalyst contains tin. The tin serves to further suppress isomerization of the paraffins. Preferably, the catalyst contains tin at an atom ratio with said Group VIII metal of 1:4 to 2:1, more preferably about 1:1.

The term "selectivity", as used in the present invention, is defined as the percentage of moles of paraffins converted to olefins relative to moles converted to olefins, isomers, and cracked products, $$\text{i.e., Selectivity} = \frac{100 \times \text{moles of paraffins converted to olefins}}{\text{moles of paraffins converted to olefins isomers, \& cracked products}}$$

This selectivity is a measure of the efficiency of the process in converting paraffins to olefins as opposed to the less desirable products of isomerization and cracking.

Feedstock

A wide range of paraffinic hydrocarbons can be used as feedstock for the present invention. Representative useful hydrocarbon feeds include petroleum refinery streams such as paraffin wax cuts, isoparaffin fractions, $C_6$-$C_{10}$ saturated hydrocarbon cuts, ethylbenzene concentrates, and the like. Preferably, the feedstock comprises $C_3$ paraffins, $C_4$ paraffins, $C_5$ paraffins, and mixtures thereof. The present invention is especially useful for the dehydrogenation of isobutane to isobutene.

Dehydrogenation Reaction

According to the present invention, the hydrocarbon feed is contacted with the catalyst in a fixed bed system, a moving bed system, a fluidized system, or in a batch-type operation. In view of the danger of attrition losses of the valuable catalyst, it is preferred to use either a fixed bed system or a dense-phase moving bed system. In a fixed bed system, the hydrocarbon feed is preheated by any suitable heating means to the desired reaction temperature and then is passed into a dehydrogenation zone containing a fixed bed of the catalyst. The dehydrogenation zone may be one or more separate reactors with suitable means therebetween to ensure that the desired conversion temperature is maintained at the entrance to each reactor. The reactants may be contacted with the catalyst bed in either upward, downward, or radial flow fashion.

In accordance with the present invention, a dehydrogenatable hydrocarbon is contacted with a sulfided, large-pore zeolite containing at least one Group VIII metal. Reaction temperatures are in the range of from 850° F. to 1250° F., preferably from about 900° F. to 1150° F. Reaction pressures are less than 20 psig, preferably in the range of from 0.1 to 1 atmosphere. For best results, the liquid hourly space velocity is below 40, and the H$_2$/HC is less than 10.

The dehydrogenation catalyst according to the invention is a sulfided, large-pore zeolite charged with one or mor dehydrogenating constituents. The term "large-pore zeolite" is defined as a zeolite having an effective pore diameter of 6 to 15 Angstroms.

Type L zeolite, zeolite X, zeolite Y and faujasite are thought to be the best large-pore zeolites for this operation and have apparent pore sizes on the order of 7 to 9 Angstroms.

The chemical formula for zeolite Y expressed in terms of moles of oxides may be written as:

(0.7–1.1)Na$_2$O:Al$_2$O$_3$:xSiO$_2$:yH$_2$O wherein x is a value greater than 3 up to about 6 and y may be a value up to about 9. Zeolite Y is described in more detail in U.S. Pat. No. 3,130,007, which is hereby incorporated by reference to show a zeolite useful in the present invention.

Zeolite X is a synthetic crystalline zeolitic molecular sieve which may be represented by the formula:

(0.7–1.1)M$_{2/n}$O:Al$_2$O$_3$:(2.0–3.0)SiO$_2$:yH$_2$O wherein M represents a metal, particularly alkali and alkaline earth metals, n is the valence of M, and y may have any value up to about 8 depending on the identity of M and the degree of hydration of the crystalline zeolite. Zeolite X is described in more detail in U.S. Pat. No. 2,882,244, which is hereby incorporated by reference to show a zeolite useful in the present invention.

A preferred catalyst according to the invention is a sulfided, type L zeolite charged with one or more dehydrogenating constituents. Type L zeolites are synthetic zeolites. A theoretical formula is M$_{9/n}$ [(AlO$_2$)$_9$(SiO$_2$)$_{27}$]  in which M is a cation having the valency n. The real formula may vary without changing the crystalline structure; for example, the mole ratio of silicon to aluminum (Si/Al) may vary from 1.0 to 3.5. U.S. Pat. No. 3,216,789 is hereby incorporated by reference to show a type L zeolite useful in the present invention.

Alkaline Earth Metals

A possible element of the present invention is the presence of an alkaline earth metal in the catalyst. That alkaline earth metal can be either barium, strontium or calcium. Preferably the alkaline earth metal is barium. The alkaline earth metal can be incorporated into the zeolite by synthesis, impregnation or ion exchange. Barium is preferred to the other alkaline earths because the resulting catalyst has high activity, high selectivity and high stability.

In one embodiment, at least part of the alkali metal is exchanged with barium, using techniques known for ion exchange of zeolites. This involves contacting the zeolite with a solution containing excess Ba$^{++}$ ions, preferably in excess of the zeolite exchange capacity. The barium should preferably constitute from 0.1% to 35% of the weight of the zeolite, more preferably from 1% to 20% by weight.

Group VIII Metals

The dehydrogenation catalysts according to the invention are charged with one or more Group VIII metals, e.g., nickel, ruthenium, rhodium, palladium, iridium or platinum.

The preferred Group VIII metals are iridium and particularly platinum, which are more selective with regard to dehydrogenation than other Group VIII metals. The preferred percentage of platinum in the catalyst is between 0.1% and 5%, more preferably from 0.1% to 1.5%.

Group VIII metals can be introduced into the zeolite by synthesis, impregnation or exchange in an aqueous solution of an appropriate salt. When it is desired to introduce two Group VIII metals into the zeolite, the operation may be carried out simultaneously or sequentially.

By way of example, platinum can be introduced by impregnating the zeolite with an aqueous solution of tetrammineplatinum (II) nitrate, tetrammineplatinum (II) hydroxide, dinitrodiamino-platinum or tetrammineplatinum (II) chloride. In an ion exchange process, platinum can be introduced by using cationic platinum complexes such as tetrammineplatinum (II) nitrate.

Tin

Preferably, the dehydrogenation catalyst contains tin. The tin exhibits a differential inhibitory effect upon the several catalytic activities of the Group VIII metals. In the case of platinum, the tin effect is especially useful in that sulfided composites of tin, platinum, and large-pore zeolite can exhibit dehydrogenation catalytic activities for hydrocarbons to the virtual exclusion of their otherwise known isomerization and cracking activities.

Representative useful tin compounds include tetrabutyl, phenyl, ethyl, propyl, octyl, decyl, tin and the like, as well as diphenyl, dipropyl, dioctyl, and the like organometallic tin compounds. These compounds may be formulated as follows: Sn(R)$_n$ in which n may be 2 or 4 and R is a hydrocarbon radical containing from 1 to 20 carbon atoms. The several R's in a given compound may be the same or different.

Also useful as tin compounds are the organometallic halides of the form Sn(R)$_n$X$_{4-n}$ where Sn has a valence state of +4; R is a hydrocarbon radical containing from 1 to 6 carbon atoms; X is a halide selected from Cl$^-$, Br$^-$, F$^-$ and I$^-$; and n is from 1 to 3. Also useful as tin compounds are the organometallic halides of the form Sn(R)X; where Sn has a valence state of +2. For co-impregnation with platinum in an aqueous media, preferably the tin compound is the halide SnX$_4$ or SnX$_2$, acetate or nitrate.

Catalyst Pellets

The catalyst can be bound with a carrier to give the catalyst strength. The carrier can be a natural or a synthetically produced inorganic oxide or combination of inorganic oxides. Preferred loadings of inorganic oxide are from 5% to 50% by weight of the catalyst. Typical acidic inorganic oxide supports which can be used include silica, alumina and aluminosilicates.

In one embodiment, the zeolite is made, then the zeolite is ion exchanged with a barium solution, separated from the barium solution, dried and calcined, impregnated with platinum, dried and calcined, impregnated with tin, dried, calcined and optionally reduced in hydrogen at about 900° F., and then mixed with the inorganic oxide and extruded through a die to form cylindrical pellets, then the pellets are dried and calcined.

In another embodiment, the large-pore zeolite is mixed with the inorganic oxide and extruded through the die to form cylindrical pellets, then the pellets are dried and calcined, then these pellets are ion exchanged with a barium solution, separated from the barium solution, impregnated with platinum, separated from the platinum solution dried and calcined, impregnated with tin, dried and calcined.

In a third embodiment, one of the two above procedures is carried out, but with co-impregnation of platinum and tin. This reduces the number of handling steps.

In one embodiment, a dehydrogenation catalyst is used which comprises (1) a sulfided, type L zeolite containing from 8% to 10% by weight barium, from 0.6% to 1.0% by weight platinum, and tin at an atom ratio with said platinum of about 1:1; and (2) an inorganic binder selected from the group consisting of silica, alumina, and aluminosilicates. Isobutane is contacted with this dehydrogenation catalyst in the presence of a sulfurcontaining gas at a temperature of from 850° F. to 1250° F., a pressure of less than 20 psig, a liquid hourly space velocity of below 40, and an $H_2$/HC of less than 10. The resulting product stream is mostly isobutene, with small amounts of propane and propylene being the main by-products by weight. Since these $C_3$ by-products have different boiling points than isobutene, they can be readily separated from the product stream by distillation.

EXAMPLES

The invention will be further illustrated by the following examples which set forth particularly advantageous method and composition embodiments. While the examples are provided to illustrate the present invention, they are not intended to limit it.

EXAMPLE 1

A catalyst was prepared by (1) ion exchanging a potassium-barium-type L zeolite with a sufficient volume of 0.17 molar barium nitrate solution to contain an excess of barium compared to the ion exchange capacity of the zeolite; (2) drying the resulting barium-exchanged type L zeolite catalyst; (3) calcining the catalyst at 590° C.; (4) impregnating the catalyst with 0.8% platinum using tetrammineplatinum (II) nitrate; (5) drying the catalyst; (6) calcining the catalyst at 260° C.; and (7) reducing the catalyst in hydrogen at 480° C. to 500° C.

EXAMPLE 2

The catalyst of Example 1 was loaded into a ¼" stainless steel reactor tube, reduced for 2 hours at 900° F. in flowing hydrogen, and used to convert isobutane at 900° F., 0 psig, 0.75 LHSV, and 6 $H_2$/HC. Conversion was nearly 100%, with 82% converted to methane and 17% to ethane.

EXAMPLE 3

Figure 2:
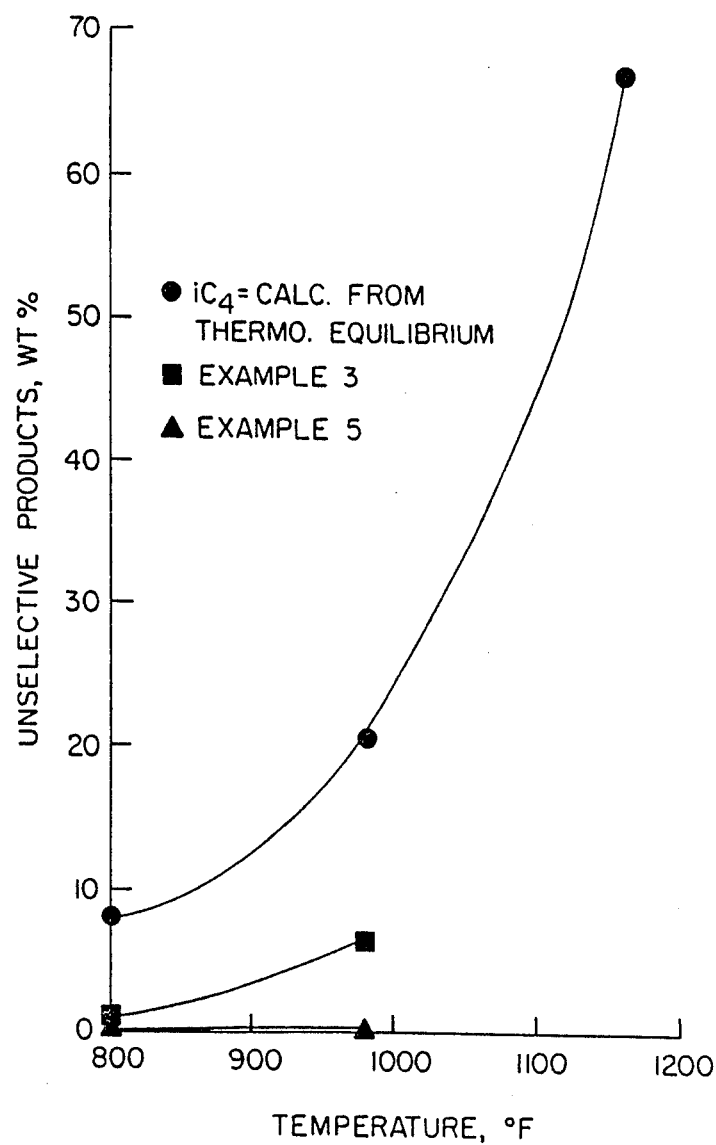
FIG. 2 is a graph showing the percent unselective products produced with catalysts of the present invention at various temperatures.

To the catalyst of Example 2, $H_2S$ was added by introducing the $H_2S$ into the hydrogen line ahead of the reactor. The atomic ratio of sulfur added to platinum was about 1:3. With isobutane at the conditions in Example 2, methane production was almost totally eliminated and isobutene production was near the thermodynamic equilibrium amount, but there were still unselective products made, even at 1:1 S/Pt, due mostly to feed isomerization to n-butane. The percent isobutene produced and percent unselective products as functions of reaction temperature are shown in FIGS. 1 and 2, respectively, after sulfur addition at about 1:1 with platinum.

EXAMPLE 4

The catalyst of Example 1 was impregnated to 0.5 wt % Sn by the pore-fill method using a solution of $(C_4H_9)_3SnCl$ in pentane. The catalyst was dried at 150°0 F., packed into a reactor, and calcined in air at 900° F. for 2 hours. The catalyst was then reduced and tested as in Example 2. The $C_1$-$C_2$ production at 900° F. was nearly 30 wt %.

EXAMPLE 5

The catalyst of Example 4, which contained both platinum and tin, was treated with $H_2S$ as in Example 3. Feed isomerization was nearly absent, such that isobutene selectivity was greatly improved (see FIGS. 1 and 2). This clearly shows the benefit of adding both tin and sulfur to the Group VIII metal-containing catalyst.

EXAMPLE 6

Another catalyst was prepared as in Example 4. After reduction in hydrogen and sulfiding, it was tested for isobutane dehydrogenation at 1100° F., 15 psig, 0.75 LHSV, and 6 $H_2$/HC. The product composition is shown in the following table:

TABLE I

| Product | Weight % |
|---|---|
| $C_1$-$C_2$ | 0.7 |
| $C_3$ | 1.8 |
| $iC_4$ | 63.6 |
| $iC_4=$ | 33.6 |
| $nC_4$ | 0.2 |
| $2$-$C_4=$ | 0.1 |
| | 100.0 |

While the present invention has been described with reference to specific embodiments, this application is intended to cover those various changes and substitutions which may be made by those skilled in the art without departing from the spirit and scope of the appended claims.

What is claimed is:

1. A method of producing isobutene from isobutane comprising contacting said isobutane with a dehydrogenation catalyst in the presence of a sulfur-containing gas at a temperature of from 850° F. to 1250° F., a pressure of less than 20 psig, a liquid hourly space velocity of below 40, and an $H_2$/HC of less than 10; wherein said dehydrogenation catalyst comprises:
    (a) a sulfided, L zeolite containing from 8% to 10% by weight barium, from 0.6% to 1.0% by weight platinum, and tin at an atom ratio with said platinum of about 1:1; and
    (b) an inorganic binder selected from the group consisting of silica, alumina, and aluminosilicates.

2. A dehydrogenation process comprising contacting a paraffinic feed with a dehydrogenation catalyst at conditions which favor dehydrogenation to produce an olefin product stream; wherein said dehydrogenation catalyst comprises a sulfided, L zeolite containing an alkaline earth metal, tin and a Group VIII metal selected from the group consisting of platinum or iridium.

3. A dehydrogenation process according to claim 2 wherein said dehydrogenation catalyst contains tin at an atom ratio with said Group VIII metal of from 1:4 to 2:1.

4. A dehydrogenation process according to claim 2 wherein said paraffinic feed contains paraffins selected from the group consisting of $C_3$ paraffins, $C_4$ paraffins, $C_5$ paraffins, and mixtures thereof.

5. A dehydrogenation process according to claim 4 wherein said paraffinic feed comprises isobutane and said olefin product stream comprises isobutene.

6. A dehydrogenation process according to claim 5 wherein said paraffinic feed is contacted with said dehydrogenation catalyst at a temperature of from 850° F. to 1250° F., a pressure of less than 20 psig, a liquid hourly space velocity of below 40, and an $H_2$/HC of less than 10.

7. A dehydrogenation process according to claim 2 wherein said paraffinic feed is contacted with said dehydrogenation catalyst in the presence of a sulfur-containing gas.

8. A dehydrogenation process according to claim 2 wherein said alkaline earth metal is selected from the group consisting of barium, strontium, and calcium.

9. A dehydrogenation process according to claim 8 wherein said alkaline earth metal is barium.

10. A dehydrogenation process according to claim 9 wherein said catalyst has from 8% to 10% by weight barium and from 0.6% to 1.0% by weight platinum.

* * * * *